(12) United States Patent
Sabo et al.

(10) Patent No.: US 11,759,187 B2
(45) Date of Patent: Sep. 19, 2023

(54) FOOTSWITCH FOR MEDICAL DEVICES

(71) Applicant: KARL STORZ SE & CO KG, Tuttlingen (DE)

(72) Inventors: Alexander Sabo, Tuttlingen (DE); Carina Zimmermann, Tuttlingen (DE)

(73) Assignee: KARL STORZ SE & CO KG, Tuttlingen (DE)

( * ) Notice: Subject to any disclaimer, the term of this patent is extended or adjusted under 35 U.S.C. 154(b) by 241 days.

(21) Appl. No.: 17/023,729

(22) Filed: Sep. 17, 2020

(65) Prior Publication Data

US 2021/0085299 A1 Mar. 25, 2021

(30) Foreign Application Priority Data

Sep. 23, 2019 (DE) ...................... 10 2019 125 490.6

(51) Int. Cl.
*A61B 17/00* (2006.01)
*A61B 90/00* (2016.01)

(52) U.S. Cl.
CPC .............. *A61B 17/00* (2013.01); *A61B 90/36* (2016.02); *A61B 2017/00115* (2013.01);
(Continued)

(58) Field of Classification Search
CPC .......... A61B 17/00; A61B 2017/00115; A61B 2017/00212; A61B 2017/00221; A61B 2017/00973; A61B 90/36; A61B 1/00; A61B 3/00; A61B 5/00; A61B 6/00; A61B 7/00; A61B 8/00; A61B 9/00; A61B 10/00; A61B 13/00; A61B 16/00; A61B 18/00; A61B 34/00; A61B 42/00; A61B 46/00; A61B 50/00; A61B 90/00; A61B 2217/00; A61B 2218/00; A61B 2503/00;
(Continued)

(56) References Cited

U.S. PATENT DOCUMENTS 5,635,777 A * 6/1997 Telymonde .............. H01H 3/14
73/146
5,758,267 A * 5/1998 Pinder .................... H04B 1/401
341/20

(Continued)

FOREIGN PATENT DOCUMENTS

DE 19640267 A1 4/1997

OTHER PUBLICATIONS

European Search Report for European Patent Application No. 20197773.3, dated Jan. 26, 2021.
(Continued)

*Primary Examiner* — Peter D Le
(74) *Attorney, Agent, or Firm* — Jason H. Vick; Sheridan Ross, PC

(57) ABSTRACT

A foot switch (1, 26) for use with a medical device (16, 27, 28) comprises an interface (10) for a communications link between the foot switch (1, 26) and a control unit (12) of the device (16, 27, 28) and comprises at least one pedal (2, 3) for operating the foot switch (1, 26) using a foot. An operation sensor (17) captures an operation of the foot switch (1, 26) for switching a function of the medical device (16, 27, 28). The control unit (12) assigns the function to the pedal (2, 3) via the interface (10) and the assigned function is displayed on the foot switch (1, 26) by a multicolor LED (4, 5).

21 Claims, 2 Drawing Sheets

(52) U.S. Cl.
CPC ............... *A61B 2017/00212* (2013.01); *A61B 2017/00221* (2013.01); *A61B 2017/00973* (2013.01)

(58) Field of Classification Search
CPC ............ A61B 2505/00; A61B 2560/00; A61B 2562/00; A61B 2576/00
See application file for complete search history.

(56) References Cited

U.S. PATENT DOCUMENTS

| | | | | |
|---|---|---|---|---|
| 5,883,615 | A * | 3/1999 | Fago | H01H 3/14 307/119 |
| 6,618,039 | B1 * | 9/2003 | Grant | G06F 3/0238 345/169 |
| 6,666,860 | B1 * | 12/2003 | Takahashi | A61B 17/320068 606/34 |
| 7,557,317 | B2 | 7/2009 | Blaha et al. | |
| 10,201,382 | B2 * | 2/2019 | Wiener | H01L 41/042 |
| 10,503,199 | B1 * | 12/2019 | Cone | G05G 1/305 |
| RE47,996 | E * | 5/2020 | Turner | A61N 7/00 |
| 10,639,104 | B1 * | 5/2020 | Barral | A61B 34/20 |
| 2002/0070840 | A1 * | 6/2002 | Fischer | H01H 3/14 338/5 |
| 2005/0070800 | A1 * | 3/2005 | Takahashi | A61B 90/98 600/459 |
| 2006/0043860 | A1 * | 3/2006 | Haba | H01J 31/126 313/310 |
| 2007/0227868 | A1 * | 10/2007 | Blaha | H01H 9/182 200/310 |
| 2009/0021476 | A1 * | 1/2009 | Steinle | G16H 40/63 345/156 |
| 2009/0046146 | A1 * | 2/2009 | Hoyt | A61B 1/0004 345/169 |
| 2009/0076368 | A1 * | 3/2009 | Balas | A61B 1/042 600/407 |
| 2010/0198200 | A1 * | 8/2010 | Horvath | G05G 1/305 606/1 |
| 2011/0304778 | A1 * | 12/2011 | Roberts | H04N 21/42213 709/203 |
| 2012/0081845 | A1 * | 4/2012 | Yato | G06F 1/1626 361/679.01 |
| 2013/0168212 | A1 * | 7/2013 | Tseng | H01H 9/26 200/86.5 |
| 2013/0172906 | A1 * | 7/2013 | Olson | A61B 34/30 606/130 |
| 2013/0225986 | A1 * | 8/2013 | Eggers | A61B 8/4444 600/425 |
| 2013/0335992 | A1 * | 12/2013 | Jaffe | G02B 27/141 362/583 |
| 2014/0364864 | A1 * | 12/2014 | Lynn | G05G 1/305 606/107 |
| 2016/0088383 | A1 * | 3/2016 | Yan | H04R 5/0335 381/378 |
| 2016/0177844 | A1 * | 6/2016 | Fuentes Utrilla | F02D 31/001 701/110 |
| 2016/0220324 | A1 * | 8/2016 | Tesar | A61B 90/361 |
| 2016/0235432 | A1 * | 8/2016 | Akagane | A61B 18/1442 |
| 2016/0317243 | A1 * | 11/2016 | Garcia Coni | A61G 13/121 |
| 2016/0367326 | A1 * | 12/2016 | Schröck | A61C 3/025 |
| 2017/0202628 | A1 * | 7/2017 | Dell | A61B 34/30 |
| 2017/0327371 | A1 * | 11/2017 | Bai | H04W 4/029 |
| 2017/0347979 | A1 * | 12/2017 | Fehre | G06F 30/13 |
| 2019/0183703 | A1 * | 6/2019 | Paul | A61G 7/012 |
| 2020/0022761 | A1 * | 1/2020 | Cone | A61B 34/74 |
| 2020/0163731 | A1 * | 5/2020 | Itkowitz | A61B 1/00193 |
| 2020/0312012 | A1 * | 10/2020 | Ishii | G06T 15/08 |
| 2020/0323540 | A1 * | 10/2020 | Kang | A61B 17/15 |
| 2021/0030497 | A1 * | 2/2021 | Daley | A61B 90/361 |

OTHER PUBLICATIONS

German Search Report for German Patent Application No. 102019125490.6, dated Jun. 9, 2020.

* cited by examiner

FOOTSWITCH FOR MEDICAL DEVICES

CROSS-REFERENCE TO RELATED APPLICATIONS

This application claims the benefit under 35 U.S.C. 119(a) to German Patent Application No. 10 2019 125 490.6, filed Sep. 23, 2019, the disclosure of which is incorporated herein by reference in its entirety.

SUMMARY

The present invention relates to a foot switch for controlling one or more medical devices.

Numerous medical devices have functions that can be triggered, activated and deactivated, modified, modulated or controlled in any other way by medical staff. To this end, user interfaces are provided on medical devices or the medical devices are able to be coupled with user interfaces. Foot switches are conventional in many applications in order to allow medical staff to control one or more functions even in the case where no hands are free for a manual action at a user interface.

The prior art has disclosed the practice of coloring the pedals of medical foot switches, i.e., assigning them fixed colors which indicate the function of the pedal. For example, foot switches connected to electrosurgical devices are usually provided with blue and yellow pedals. The colors of the pedals cannot be changed.

U.S. Pat. No. 7,557,317B2 has disclosed a medical foot switch. The latter can be connected to an electrosurgical device. The housing of this foot switch can comprise one or more light sources which illuminate the pedals of the foot switch fastened to the housing. The pedals comprise LEDs (light-emitting diodes), which indicate the function of the relevant pedal. The individual LEDs can have different colors, illuminate lettering from behind or form said lettering. Likewise, a selected function of the device can be indicated on a display on the foot switch.

A disadvantage of this foot switch known from the prior art is that only a very restricted number of functions can be displayed and distinguished by the LEDs. Secondly, the provision of a display for displaying text on the foot switch is very complicated and expensive.

It is therefore an object of the present invention to develop an improved foot switch, to which a large number of different functions can be assigned.

This object is achieved by an apparatus and a medical system according to the claims herein.

Advantageous developments of the invention emerge from the dependent claims.

A foot switch according to the invention for use with a medical device comprises an interface for a communications link between the foot switch and a control unit of the device. At least one pedal of the foot switch allows the latter to be operated by a user using a foot. An operation sensor captures the operation of the foot switch in order thus to switch a function of the medical device. To this end, the operation sensor generates an appropriate signal, for example electrical signal, which is transmitted via the interface to the control unit of the device and which triggers the switching of the function of the device there. Further, the foot switch comprises a processor, which is embodied to receive signals from the control unit, which assign the function to be switched to the at least one pedal, via the interface. Moreover, an LED is arranged on the foot switch, for displaying the associated function in a certain color. Here, the LED is a multicolor LED, which can generate light in a multiplicity of different colors. In this way, the different functions of the device respectively assigned to the foot switch are each displayed in a certain color by the LED.

The foot switch can comprise one, two or more pedals, which control the device linked via the interface or individual functions of this device. By way of example, foot switches with two pedals are conventional. By way of example, the pedal is embodied as a rocker, with a tread, by means of which the user can operate the pedal using the foot. Operating the pedal, i.e., moving the tread, is captured by one or more sensors. By way of example, Hall sensors have proven their worth in this case, in particular such Hall sensors that can precisely capture a magnetic field change. The sensors can be provided multiple times in order to compare signals with one another and avoid malfunctions to ensure the patient's safety. Foot switches can comprise pressure points such that a resistance has to be overcome when operating the pedal, said resistance giving the user a better feeling for the operation of the pedal and avoiding an inadvertent operation. The foot switch can be supplied with power via a cable or else comprise a dedicated power source such as a battery.

In medicine, there are a multiplicity of devices that can be controlled by way of foot switches, for example pumps for liquids, insufflators for the insufflation of gas, pinch valves, camera systems, light sources, devices for documenting medical interventions, devices for electrosurgery, controllers for lasers, motors or lithotripters. The functions to be controlled are relevant to the health of the patient and potentially hazardous, and so a correct operation of the devices is of great importance.

The foot switch and device, or the control unit thereof, can be linked via the interface on the foot switch for communication purposes and for the exchange of signals, either via cables or else in wireless fashion. In the case of a wireless link, the control unit will ensure within the scope of the communication with the foot switch that the correct foot switch is connected and only the latter may switch the device. Additionally, a person skilled in the art will provide a means to monitor the correct link between device and foot switch. By way of example, if the wireless connection drops, the function of the device can be deactivated or stopped for safety reasons.

According to the invention, provision is now made for the control unit in the connected device to be configured to assign a function of the device, which should be controlled or switched by the pedal, to the at least one pedal of the foot switch via the interface provided for communication purposes. To this end, the signals are guided via the interface to the processor of the foot switch. Thus, the foot switch is a universally employable foot switch, which has no fixed function assigned in advance; instead, a function is assigned to said foot switch depending on the application and device by way of the connected device. This can be implemented automatically by the control unit of the device when the foot switch is connected to the device. Alternatively, one or more functions for the one or more pedals can be assigned to an already connected foot switch by a user by way of an operating unit on the device or the control unit. In another alternative, the control unit, when setting a certain mode of operation for the device, can assign the foot switch or its pedal a function that is preprogrammed to this end. In general, the control unit can be part of the medical device; however, it can also be a separate unit, which also controls even more devices in a medical system, for example. For communication purposes and for the control of the foot switch itself, the latter can comprise a microcontroller. The processor can be part of the microcontroller, as is usually provided in the case of microcontrollers. In a manner known per se, the device and the control unit can comprise processors, memory, software and operating units such as switches, touch displays or other input means.

Operating the pedal on the foot switch by the user leads to an operating signal triggered by the operation sensor, said signal being transmitted via the interface to the control unit of the device and triggering or terminating the previously assigned function there. In the present text, the term "switching" means both triggering and terminating a function or changing to another function.

Since a function can be individually assigned to each pedal of the foot switch by the control unit, provision is made for the assigned function to be indicated to the user by an LED (light-emitting diode) on the foot switch that shines in a certain color. Use is made of a multicolor LED, which can shine in many different colors. Thus, depending on the function of the device, the multicolor LED can shine in a certain color and communicate the function assigned to the pedal to the user. Thus, each function can be illustrated by a dedicated color, even though only a single LED is used. Many different functions of the device or of a plurality of linked devices can be alternately assigned to the foot switch or the individual pedals and each can be indicated by the multicolor LED by a dedicated color. These can be specified colors, which are usually assigned to the desired functions or which are specified by a standard, such as a blue and yellow for the coagulation and cutting functions for the use of foot switches in electrosurgery. However, this could also be a color individually selected by the user, which the latter manually assigns on the control unit to the specific desired function. The user will choose various colors in the case of a plurality of functions. Alternatively, colors are already preprogrammed for the various functions by the device, and these colors are communicated to the foot switch.

The multicolor LED can consist of a plurality of light-emitting diodes, in particular at least two light-emitting diodes, or this could relate to a single light-emitting diode. The light-emitting diodes can be arranged in a common LED housing. The light-emitting diodes of the multicolor LED can be linked via a common cathode or a common anode. Alternatively, the multicolor LED can comprise only two different diodes.

In particular, the multicolor LED can reproduce all colors of an RGB color space. To this end, the multicolor LED can be an RGB-LED, i.e., an LED which consists of three individual light-emitting diodes which shine with an adjustable intensity in the colors of red, green and blue and which, together, can generate all colors of an RGB color space. To this end, the three individual light-emitting diodes are operated with different intensities and combined. To the human observer, the light appears like a color that was mixed from the three primary colors. The multicolor LED and, in particular, the RGB-LED are advantageous in that a large multiplicity of functions can be distinguished and individual colors can be assigned to these functions, which colors are then displayed on the foot switch following the assignment. Hence, the foot switch is suitable for any conceivable application and can be used individually.

Thus, the pedals can be uniquely assigned to a function even in the case of a complex medical system with many devices and functions, which are intended to be controlled by way of the foot switch. Thus, the foot switch can comprise at least two pedals and two multicolor LEDs, wherein different functions are assigned to the pedals by the control unit. These functions are then indicated in color by way of the respective multicolor LED. Usually, a dedicated multicolor LED will be assigned to each pedal.

The user immediately sees the function assigned to a pedal and incorrect operation is avoided. Additionally, the foot switch can be alternately linked to different devices, particularly in the case of a wireless link, said devices assigning the respective fitting function to the pedals and indicating this at the foot switch by way of the appropriate color. This increases the flexibility of the system and the application. Additionally, each function no longer requires a separate foot switch.

The foot switch can comprise a housing, in or on which the one or more pedals are arranged. In this case, the multicolor LED can be located in the housing and can be covered by a transparent viewing window, through which a user can see the light color generated by the multicolor LED. The viewing window can be arranged in the surface of the housing and, for example, terminate flush with the latter. By way of example, the multicolor LED can be situated in a region of the housing above the pedal. Then, the viewing window is arranged in the upper side of the housing. However, other covers for the LEDs are also conceivable. Likewise, these could be situated in the tread of the pedal instead of in the housing. However, this is disadvantageous in that the colored light may no longer be seen during the operation by the foot.

Furthermore, the housing of the foot switch can comprise an additional operation switch, by means of which further functions can be switched. By way of example, this could be used to activate and deactivate the foot switch or activate and deactivate the wireless link. The switch can likewise be illuminated by an LED, in particular a multicolor LED, which illuminates the switch itself, or the switch can have an edge, for example a ring surrounding the switch, which is lit up by an LED. This allows the activation state of the foot switch or the wireless link, or else error messages, to be represented by different colors or signals such as blinking, in order to inform the user.

For the purposes of communicating between the foot switch and the device or its control unit, both parts can be linked via a medical data transmission system, in particular a BUS system. The latter, in turn, can be part of a larger medical system with many components, as is the case in an operating theater. Then, the control unit can also be part of the control of the operating theater. Provision can be made for the foot switch to be automatically identified upon activation or link to the system and functions, which are already preselected, are assigned thereto by the control unit, which functions are then indicated by the multicolor LEDs.

Alternatively, a device with a control unit and a foot switch could be linked to one another by way of other wired or wireless signal paths and the control unit can be linked to a medical system via a BUS or any other data link.

The invention therefore also comprises a medical system comprising at least two devices and at least one foot switch according to the invention, as described above, wherein the devices and the at least one foot switch are linked via a medical data transmission system and communicate via the latter.

BRIEF DESCRIPTION OF THE DRAWINGS

Further aspects of the invention arise from the following description of the preferred exemplary embodiments and the attached drawings. In detail.

DETAILED DESCRIPTION

Figure 1:
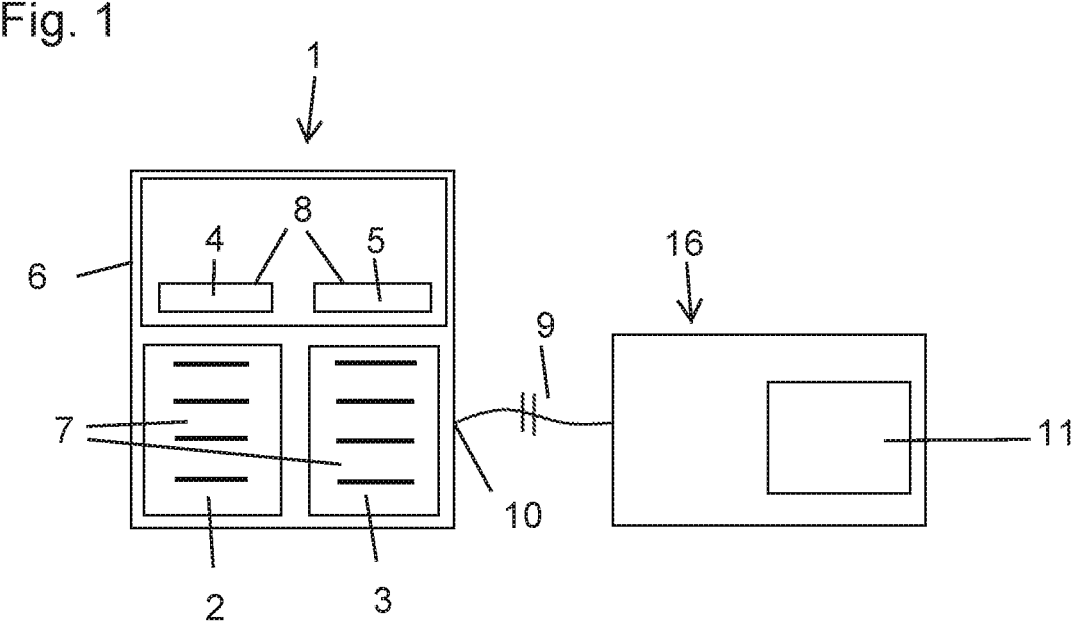
FIG. 1 shows a foot switch linked to a device
Figure 3:
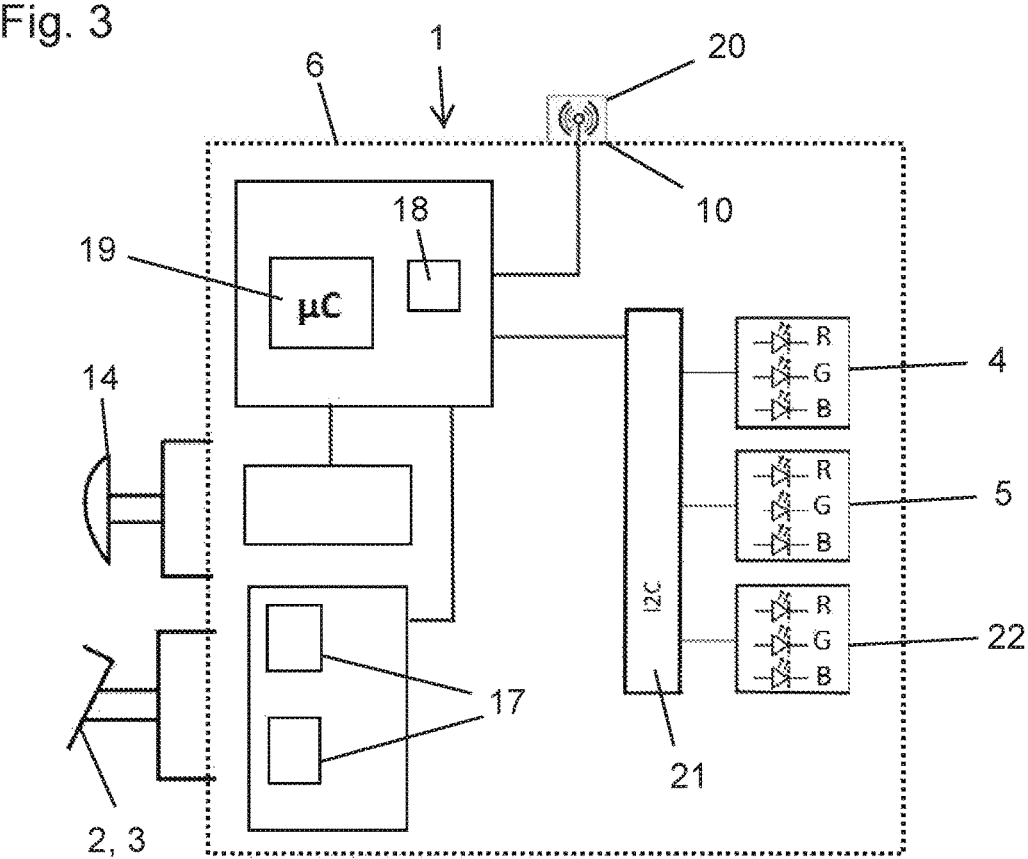
FIG. 3 shows a schematic illustration of the foot switch

FIG. 1 schematically illustrates a foot switch 1 according to the invention with a device 16 to be operated. The foot switch 1 comprises a housing 6, arranged within which are a first pedal 2 and a second pedal 3, each with a tread 7. The tread has a knurled surface to provide a better hold. Viewing windows 8, behind which a first multicolor LED 4 and a second multicolor LED 5 are located, are located in a region of the housing 6 above the pedals 2 and 3. The light of the LEDs 4 and 5 passes to the outside through the respective viewing window 8 and is identifiable to a user. The pedals 2, 3 are operated by a user with their foot in a manner known per se in order to control the device 16. To this end, the pedals 2, 3 each comprise at least one operation sensor 17, which is not illustrated in FIG. 1. The sensor 17 captures the operation of the respective pedal 2, 3 by the user and transmits the signal to a microcontroller 19 in the foot switch 1. There, the signal is processed by a processor, not illustrated separately. The design of the circuit with the various components within the foot switch 1 is schematically illustrated in FIG. 3. By way of example, the operation sensor 17 is a linear Hall sensor, which measures magnetic field changes. By way of example, the latter can precisely capture the movement of the tread 7 or the movement of a rotational shaft of the pedal 2, 3.

The foot switch 1 communicates with a linked device 16 and its control unit 12 (not illustrated here) via an interface 10 and a cable 9. By way of example, this device 16 can be a medical suction pump, which serves to remove unwanted liquids or gases from a body cavity. The user operates the foot switch 1 and activates or deactivates the aspiration function of the pump 16, for example when the view into the body cavity is impaired by liquid or gas. In this example, the control unit 17 is located within the device 16 and is part of said device. A touch display 11 indicates the set power of the aspiration function of the pump.

The intended functions of the pedals 2, 3 of the foot switch 1 are communicated to the foot switch 1 by the control unit 12 via the interface 10. To this end, the foot switch 1 is configured to receive signals or commands from the control unit 12 via the interface 10. These are processed by a microcontroller 19 (see FIG. 3).

In the present example, activation of the pump is assigned to pedal 2 and deactivation is assigned to pedal 3. By way of example, the multicolor LED 4 attached above the pedal 2 shines with an orange hue while the LED 5 above the pedal 3 shines with a purple hue, for example. The RGB-LEDs used here can shine in the various colors of the RGB color space. These colors are assigned to the functions and clearly communicate to the user the function triggered in the device 16 by the operation of the pedals 2 and 3. This can avoid an incorrect operation of the device 16.

Figure 2:
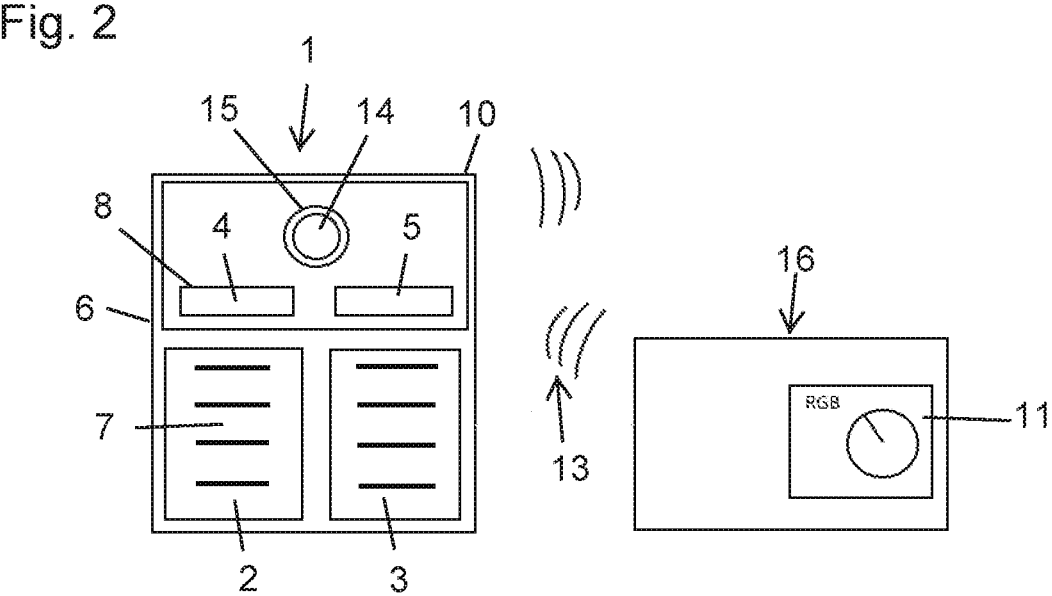
FIG. 2 shows a foot switch linked to a device in wireless fashion

FIG. 2 shows a further exemplary embodiment of a foot switch 1. The components are as described above; however, the foot switch 1 and the control unit 12 of the device 16 are not in contact via a cable, but via a wireless signal link 13. To this end, the foot switch 1 and the device 16 comprise transmitters and receivers not illustrated here. Now, the foot switch 1 additionally comprises an operation switch 14, which is arranged on the housing 6 of the foot switch 1. The switch 14 can likewise be operated by a foot and is a pressure switch, for example. Operating the switch 14 activates the foot switch 1 so that the latter is available. The operation switch 14 is surrounded by a ring 15, behind which a multicolor LED 22 is attached in turn. The ring 15 is transparent and can shine in different colors thanks to the LED 22. The status of the foot switch 1 is communicated to the user by way of different colors, for example whether the latter is currently connected to the device 16 and its control unit 12 via the wireless link 13. Optionally, the foot switch 1 may be able to switch to a sleep mode after long-term non-use. This sleep mode can likewise be indicated by way of a set color in the ring 15.

Should the user wish to assign different colors to the foot switch 1 and its pedals 2 and 3 for the "activation" and "deactivation" functions, for example to distinguish these more clearly from the colors of another foot switch or because colors are easier to identify by a user, the user can change the colors assigned to the function by way of the touch display 11 on the device 16. Since the multicolor LEDs 4 and 5 are RGB-LEDs, the colors of an RGB color space are available to the user and can be selected as required. Following the selection, the control unit 12 communicates the colors, which are assigned to the "activation" and "deactivation" functions and intended to be displayed at the pedals 2 and 3 by the LEDs 4 and 5, to the foot switch 1 via the wireless connection 13 and the interface 10. The microcontroller 19 in the foot switch 1 regulates the LEDs 4 and 5 accordingly (see also FIG. 3).

The circuit of the components within the foot switch 1 is illustrated schematically in FIG. 3. Here, the housing 6 of the foot switch 1 is indicated by a dashed line. The pedals 2, 3 and the operation switch 14 are also illustrated schematically on this housing. Each pedal 2, 3 has an assigned operation sensor 17, which reports the operation of the pedals to a microcontroller 19. Should the foot switch 1 no longer be situated in a horizontal position, as required for reliable operation of the foot switch 1, this is captured by a position sensor 18 which prompts the microcontroller 19 to deactivate the foot switch where necessary for reasons of safety. The interface 10 with the antenna 20, which facilitates the wireless communication with the device 16, is also linked to the microcontroller 19. Depending on the instructions of the control unit 12 of the device 16, the microcontroller 19 controls the RGB-LEDs 4 and 5 and the third RGB-LED 22, which is assigned to the ring 15 of the operation switch 14, via the LED-BUS 21 (I2C). The various colors of the RGB color space can be generated by a suitable control of the intensities of the individual R-, G- and B-diodes. The three diodes are arranged in a common LED housing in each case and electrically linked via a common input.

By way of example, if a fault occurs in the wireless link 13 such that reliable communication between the foot switch 1 and the device 16 is no longer ensured, the microcontroller 19 controls the LED 22 in such a way that it shines with a defined warning color and informs the user about the problem. It is understood that the operation switch 14 and the third multicolor LED 22 assigned thereto are optional and need not be provided in other embodiments, as explained in relation to FIG. 1, for example.

Figure 4:
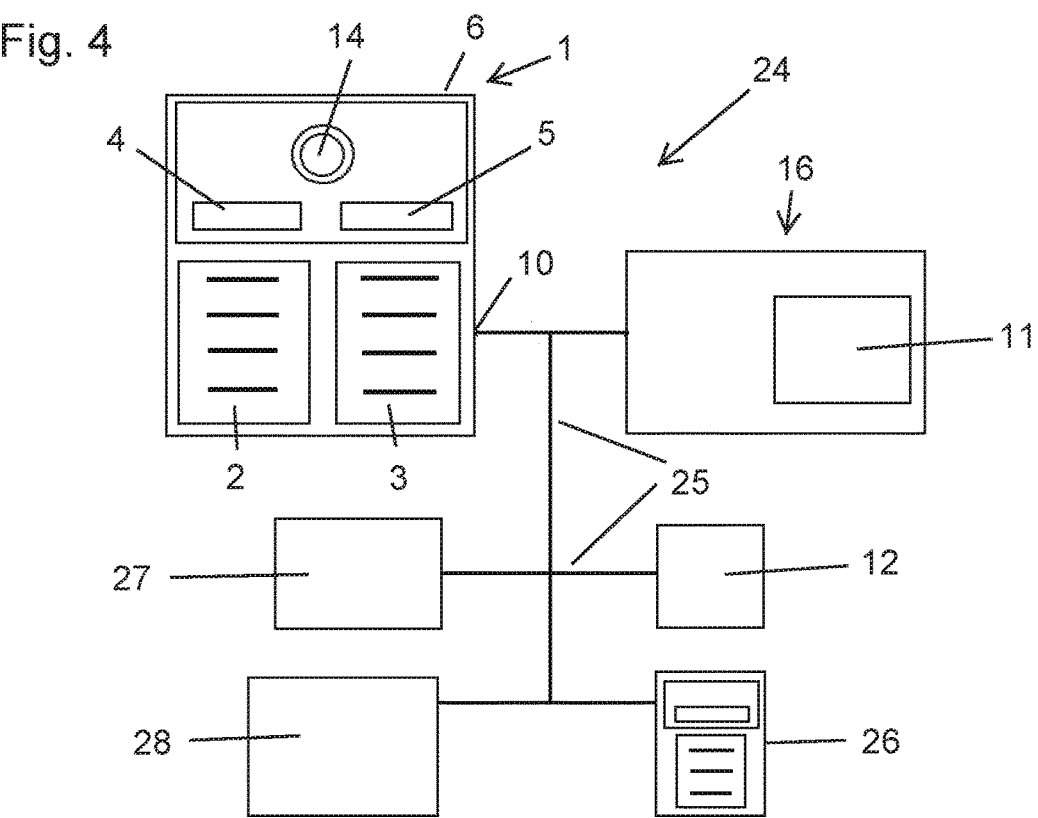
FIG. 4 shows a medical system with devices and foot switches

The particular advantages of the foot switch 1 are also exhibited in FIG. 4. Illustrated here is a medical system 24, comprising a foot switch 1 and a device 16, as described above, and comprising a second device 27, a third device 28, a control unit 12 and a second foot switch 26. According to the invention, this foot switch 26 is designed like the foot switch 1 from the exemplary embodiment of FIG. 1, albeit only having one pedal and one multicolor LED for this pedal. The other components such as housing, pedal, tread and inner structure are arranged in analogous fashion in the foot switch 26. The devices 16, 27 and 28 and the foot switches 1 and 26 are linked to one another via a medical data BUS 25. The control unit 12, which is not arranged within the device 16 in the present example but forms a separate unit with a dedicated housing, is also part of this system 24 and linked to the BUS 25. Here, the control unit 12 is an operating theater control, which accesses all devices and foot switches in the system via the BUS 25 and which controls the control of the devices via the foot switches. In particular, the control unit 12 assigns the various device functions of the devices 16, 27 and 28, which should be controlled by way of the various pedals, to the foot switches 1 and 26 via their interfaces and the BUS 25. Moreover, the control unit 12 assigns the colors, which should be displayed assigned to the pedals at the foot switches 1 and 26, to the required functions. Here, the control unit 12 can assign individual colors to the functions, either automatically or manually by way of the user, said colors rendering the functions and pedals distinguishable from one another and clearly indicating which pedal controls which function of the devices 16, 27 and 28. Where necessary, the colors and functions can be newly assigned to the foot switches 1 and 26 and their pedals. Alternatively, the control unit 12 can immediately carry out the assignment once the foot switches 1 and 26 are linked to the BUS 25 and the system 24. The system 24 can be extended as desired and can assign a large number of different functions to the foot switches 1 and 26 as provided according to the invention, said functions, characterized by different colors, being able to be displayed at the foot switches and be distinguished from one another.

LIST OF REFERENCE SIGNS

1 Foot switch
2 First pedal
3 Second pedal
4 First multicolor LED
5 Second multicolor LED
6 Housing
7 Tread
8 Viewing window
9 Cable
10 Interface
11 Touch display
12 Control unit
13 Wireless link
14 Operation switch
15 Ring
16 Device
17 Operation sensor
18 Position sensor
19 Microcontroller
20 Antenna
21 LED-BUS
22 Third multicolor LED
24 Medical system
25 BUS
26 Second foot switch
27 Second device
28 Third device

The invention claimed is:

1. A foot switch configured for use with a medical device, comprising:
an interface for a communications link between the foot switch and a control unit of the medical device,
at least one pedal configured to operate the foot switch using a foot,
an operation sensor, which is configured to capture an operation of the foot switch,
wherein the operation sensor generates a signal that is transmitted via the interface to the control unit of the medical device for the purposes of switching a function of the medical device,
a processor, in the foot switch, which is configured to receive signals from the control unit of the medical device, the signals configured to assign the function to be switched to the at least one pedal, via the interface, and
at least one LED on the foot switch configured to display the assigned function for the footswitch in a certain color of the at least one LED, wherein the LED is a multicolor LED which can generate light in a multiplicity of different colors for the purposes of displaying different assigned functions for the foot switch.

2. The foot switch as claimed in claim 1, wherein the multicolor LED comprises at least two light-emitting diodes, which comprise a common anode or a common cathode.

3. The foot switch as claimed claim 1, wherein the multicolor LED comprises at least two light-emitting diodes, which are arranged in a common LED housing.

4. The foot switch as claimed in claim 1, wherein the multicolor LED can reproduce all colors of an RGB color space.

5. The foot switch as claimed in claim 1, wherein the foot switch comprises a housing, on which the at least one pedal and the at least one multi-color LED are arranged.

6. The foot switch as claimed in claim 5, wherein the housing additionally comprises an operation switch, which is illuminated by a further light-emitting diode or which is surrounded by an edge illuminated by a further light-emitting diode.

7. The foot switch as claimed in claim 1, wherein the foot switch comprises at least two pedals and at least two multicolor LEDs and different functions can be assigned to the pedals by the control unit of the medical device and the assigned functions are each displayed by one of the multicolor LEDs.

8. The foot switch as claimed in claim 1, wherein each multicolor LED is covered by a transparent viewing window, through which a user can see the light color generated by the multicolor LED.

9. The foot switch as claimed in claim 8, wherein the viewing window is arranged in a plane of the housing.

10. The foot switch as claimed in claim 1, wherein the foot switch and the medical device are linked via a medical data transmission system and communicate via the latter.

11. A medical system comprising at least two devices and at least one foot switch as claimed in claim 1, wherein the devices and the at least one foot switch are linked via a medical data transmission system and communicate via the latter.

12. A foot switch configured to control a medical device comprising:
an interface for a communications link between the foot switch and a control unit of the medical device,
at least one pedal configured to operate the foot switch when manipulated by a foot,
a processor, in the foot switch, which is configured to receive signals, via the interface, from the control unit of the medical device, the signals configured to assign a function of the medical device to be switched by the at least one pedal to the at least one pedal, an operation sensor, which is configured to capture an operation of the foot switch when manipulated by the foot, wherein the operation sensor generates a signal that is transmitted, via the interface, to the control unit of the medical device to switch the function of the medical device, and at least one LED on the foot switch configured to display the function assigned to the footswitch by processor in a certain color of the at least one LED, wherein the LED is a multicolor LED which can generate light in a multiplicity of different colors for the purposes of displaying assigned functions of the foot switch.

13. The foot switch as claimed in claim 12, wherein the multicolor LED comprises at least two light-emitting diodes, which comprise a common anode or a common cathode.

14. The foot switch as claimed claim 12, wherein the multicolor LED comprises at least two light-emitting diodes, which are arranged in a common LED housing.

15. The foot switch as claimed in claim 12, wherein the multicolor LED can reproduce all colors of an RGB color space.

16. The foot switch as claimed in claim 12 wherein the foot switch comprises a housing, on which the at least one pedal and the at least one multi-color LED are arranged.

17. The foot switch as claimed in claim 16, wherein the housing additionally comprises an operation switch, which is illuminated by a further light-emitting diode or which is surrounded by an edge illuminated by a further light-emitting diode.

18. The foot switch as claimed in claim 12, wherein the foot switch comprises at least two pedals and at least two multicolor LEDs and different functions can be assigned to the pedals by the control unit of the medical device and the assigned functions are each displayed by one of the multicolor LEDs.

19. The foot switch as claimed in claim 12, wherein each multicolor LED is covered by a transparent viewing window, through which a user can see the light color generated by the multicolor LED.

20. The foot switch as claimed in claim 19, wherein the viewing window is arranged in a plane of the housing.

21. A programmable foot switch configured to control a medical device with an assignable function comprising:

a communications interface between the foot switch and a control unit of the medical device, at least one pedal configured to operate the foot switch when manipulated by a foot, a processor, in the foot switch, configured to receive a signal or command, via the interface, from the control unit of the medical device, the signals configured to assign a function of the medical device to be switched by the at least one pedal to the at least one pedal, an operation sensor configured to capture an operation of the foot switch when manipulated by the foot, wherein the operation sensor generates a control signal that is transmitted, via the interface, to the control unit of the medical device to switch the function of the medical device, and at least one LED on the foot switch configured to display the function assigned to the footswitch in a certain color, wherein the LED is a multicolor LED which can generate light in a multiplicity of different colors for the purposes of displaying the function assigned to the foot switch.

\* \* \* \* \*